United States Patent
Yang et al.

(10) Patent No.: US 9,939,402 B2
(45) Date of Patent: Apr. 10, 2018

(54) BLOOD SUGAR DETECTING METHOD AND CARTRIDGE USING SAME

(75) Inventors: Yongju Yang, Seoul (KR); Seungyeon Song, Seoul (KR); Moosub Kim, Seoul (KR); Yunhee Ku, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 196 days.

(21) Appl. No.: 14/377,662

(22) PCT Filed: Feb. 9, 2012

(86) PCT No.: PCT/KR2012/000944
§ 371 (c)(1),
(2), (4) Date: Sep. 9, 2014

(87) PCT Pub. No.: WO2013/118927
PCT Pub. Date: Aug. 15, 2013

(65) Prior Publication Data
US 2015/0001098 A1    Jan. 1, 2015

(51) Int. Cl.
*G01N 27/327* (2006.01)
*G01N 33/72* (2006.01)
*C12Q 1/54* (2006.01)
*G01N 33/49* (2006.01)
*G01N 21/78* (2006.01)

(52) U.S. Cl.
CPC ........... *G01N 27/3272* (2013.01); *C12Q 1/54* (2013.01); *G01N 21/78* (2013.01); *G01N 33/491* (2013.01); *G01N 33/72* (2013.01)

(58) Field of Classification Search
CPC .. G01N 27/3272; G01N 33/491; G01N 21/78; G01N 33/72; C12Q 1/54
USPC ................................ 204/403.14; 205/777.5
See application file for complete search history.

(56) References Cited

U.S. PATENT DOCUMENTS 7,282,179 B2 * 10/2007 Iwaki ............... B01L 3/502
                                              422/422
2007/0082331 A1    4/2007 Tanaami et al.
2007/0154351 A1    7/2007 Bae et al.
(Continued)

FOREIGN PATENT DOCUMENTS

KR    10-0662021 B1    12/2006
KR    2007-101428 A     4/2007
(Continued)

*Primary Examiner* — Tamir Ayad
(74) *Attorney, Agent, or Firm* — Birch, Stewart, Kolasch & Birch, LLP

(57) ABSTRACT

Disclosed are a blood sugar detecting method and a cartridge using same. A cartridge according to the present invention comprises: a blood receiving unit for receiving blood injected therein; a separation unit for separating the received blood into glucose and hemoglobin; a first measuring unit for measuring the concentration of the separated glucose; a second measuring unit for measuring the concentration of hemoglobin A1c (HbA1c) in the hemoglobin; and a third measuring unit connected to a second channel, for measuring the total concentration of hemoglobin. According to the present invention, both glucose providing short-term information on blood sugar and hemoglobin A1c providing long-term information on blood sugar can be detected by a single cartridge, thus increasing the efficiency of diabetes management.

7 Claims, 8 Drawing Sheets

(56) References Cited

U.S. PATENT DOCUMENTS

2010/0025264 A1* 2/2010 Yuan .................... C12Q 1/005
  205/777.5
2010/0299072 A1* 11/2010 Kamata .............. G01N 33/5438
  702/19

FOREIGN PATENT DOCUMENTS

| KR | 10-0776394 B1 | 11/2007 |
| KR | 10-2009-0107165 A | 10/2009 |
| KR | 10-2011-0006833 A | 1/2011 |

* cited by examiner

BLOOD SUGAR DETECTING METHOD AND CARTRIDGE USING SAME

TECHNICAL FIELD

The teachings in accordance with exemplary and non-limiting embodiments of this invention relate generally to a method for determination of glucose and HbA1c and a cartridge using the same, and more particularly to a method for determination of glucose and HbA1c, capable of measuring both a short-term blood sugar level change and a long-term blood sugar level change for enhancing efficiency of urine sugar management, and a cartridge using the same.

BACKGROUND ART

Recently, diagnostic equipment capable of conveniently diagnosing a patient health has been researched and actively commercialized. As a result, a patient current health state can be diagnosed regardless of time and place that used to be diagnosed by personally visiting a hospital and receiving a medical diagnosis. In addition, diagnosis that has no big difference in terms of reliability from direct medical diagnosis has become available due to miniaturization and accuracy of diagnosis equipment.

Diabetes greatly needs accuracy-enhanced diagnosis equipment in terms of user convenience and accuracy in diagnosis result because diabetes must be under dietary control while checking daily blood sugar. Methods measuring blood sugar in a body include a method using urine and a method using blood. Among these methods, blood sugar diagnostic equipment configured to measure blood glucose contents in blood by collecting a predetermined amount of blood from a patient has advanced greatly in terms of research to greatly enhance accuracy and reliability and to provide a great satisfaction to a user.

Conventional blood sugar diagnostic equipment measures an amount of glucose in blood using an optical method or an electrochemical method. However, a simple measurement of an amount of glucose is not sufficient for measuring blood sugar of a patient. Rather, it would be better to measure an amount of HbA1c in blood in long terms for management of health of a diabetic patient. Nevertheless, only a temporary blood sugar state can be learned by measurement of glucose alone contained in the blood. In a nutshell, it is difficult to accomplish a long term health management of a diabetic using the conventional blood sugar diagnostic equipment.

DISCLOSURE

Technical Problem

Accordingly, the present invention is disclosed in consideration of the above-mentioned problems and it is an object of the present invention to provide a method for determination of glucose and HbA1c (glycosylated hemoglobin), capable of obtaining short term information and long term information on blood sugar using a single piece of cartridge so as to effectively manage the blood sugar, and a cartridge using the same.

In one general aspect of the present invention, there is provided a cartridge, the cartridge comprising:
a blood injection unit configured to receive blood;
an elution unit configured to elute glucose and hemoglobin (Hb) from the injected blood;
a first measurement unit configured to measure concentration of the eluted glucose;
a second measurement unit configured to measure concentration of HbA1c in the hemoglobin; and
a third measurement unit configured to measure a total concentration of the hemoglobin by being connected to the second measurement unit.

Preferably, but not necessarily, the cartridge may further comprise an elution solution supply unit configured to supply an elution solution for eluting the hemoglobin alone from the injected blood by being connected to the elution unit.

Preferably, but not necessarily, the elution unit may include a membrane configured to filter the glucose alone from the injected blood.

Preferably, but not necessarily, the elution unit may further include an O-ring configured to fix the membrane.

Preferably, but not necessarily, the membrane may include a first layer consisting of nitrocellulose compound and a second layer consisting of nylon.

Preferably, but not necessarily, the blood injection unit may supply, to the injected blood, a hydrolysis solution for hydrolyzing the injected blood, and zinc for capturing only a particular material inside the blood.

Preferably, but not necessarily, the first measurement unit may measure concentration of glucose using an optical method subsequent to performance of glucose oxidase reaction.

Preferably, but not necessarily, the third measurement unit may measure a total concentration of hemoglobin using an optical method.

Preferably, but not necessarily, the second measurement unit may further include a detection electrode configured to measure concentration of HbA1c in the hemoglobin in an electrochemical method Preferably, but not necessarily, the second measurement unit may further include a glucose oxidase administration unit configured to administer glucose oxidase having an electrochemical activity to HbA1c in order to measure the concentration of HbA1c by an electrochemical method.

Preferably, but not necessarily, the cartridge may further comprise an analyzer configured to analyze blood sugar changes in the injected blood by computing a percentage concentration (% concentration) of the HbA1c based on a result of the second measurement unit and a result of the third measurement unit.

In another general aspect of the present invention, there is provided a glucose and HbA1c detecting method, the method comprising:
injecting a blood;
eluting glucose and hemoglobin (Hb) from the injected blood;
moving the eluted glucose and the hemoglobin using mutually different channels;
measuring a total concentration of the eluted hemoglobin and concentration of HbA1c in the eluted hemoglobin;
computing a percentage concentration of the HbA1c based on the total concentration of the hemoglobin and the concentration of the HbA1c; and
analyzing blood sugar changes in the injected blood, based on the computed percentage concentration (% concentration).

Preferably, but not necessarily, the method may further comprise detecting concentration of eluted glucose subsequent to the moving.

Preferably, but not necessarily, the detecting may be performed by an optical method subsequent to performance of glucose oxidase reaction.

Preferably, but not necessarily, the method may further comprise supplying, to the injected blood, a hydrolysis solution for hydrolyzing the injected blood, and zinc for capturing only a particular material inside the blood.

Preferably, but not necessarily, the measuring may include measuring a total concentration of eluted hemoglobin by an optical method, and measuring the concentration of HbA1c by an electrochemical method.

Preferably, but not necessarily, the measuring may further include administering glucose oxidase having an electrochemical activity to HbA1c in order to measure the concentration of HbA1c by an electrochemical method.

Preferably, but not necessarily, the eluting may include supplying elution solution for eluting only the hemoglobin from the injected blood.

Advantageous Effects

The method for determination of glucose and HbA1c and the cartridge using the same according to the present invention have an advantageous effect in that efficiency of urine sugar management can be enhanced through simultaneous detection of glucose having short-term information on blood sugar, and HbA1c having long-term blood sugar, by using one cartridge.

BEST MODE

Figure 1:
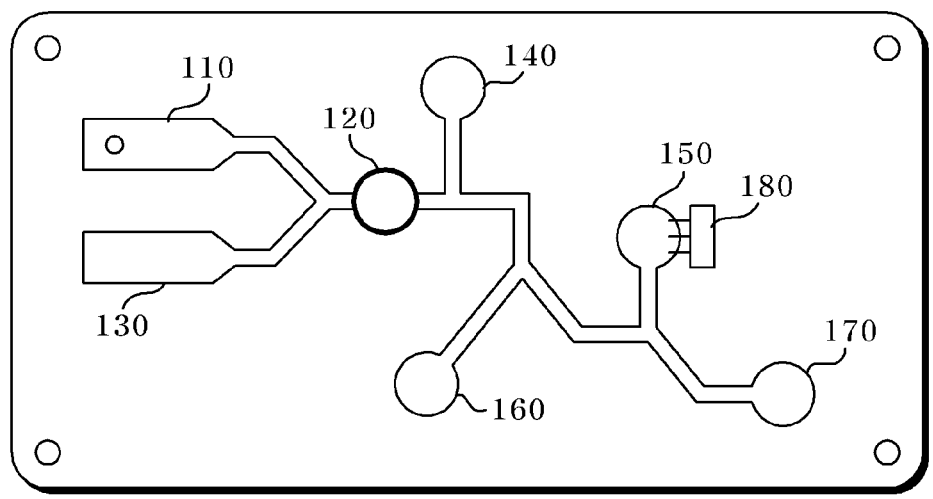
FIG. 1 is a schematic view illustrating a configuration of a cartridge according to an exemplary embodiment of the present invention.

While the invention has been described in conjunction with several specific embodiments, many further alternatives, modifications, variations and applications will be apparent to those skilled in the art that in light of the foregoing description. Thus, the invention described herein is intended to embrace all such alternatives, modifications, variations and applications as may fall within the spirit and scope of the appended claims.

It will be understood that, although the terms first, second, etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. Thus, a first element, component, region, layer, or section discussed below could be termed a second element, component, region, layer, or section without departing from the teachings of example embodiments.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Hereinafter, example embodiments of the present invention will be described in more detail with reference to the accompanying drawings. In the drawings, like reference numerals denote like elements and sizes of each element may be exaggerated for clarity and convenience of description.

FIG. 1 is a schematic view illustrating a configuration of a cartridge (100) according to an exemplary embodiment of the present invention.

The cartridge (100) according to an exemplary embodiment of the present invention is a tool configured to collect blood from a user and to measure blood sugar within the collected blood. The hemoglobin (abbreviated Hb or Hgb) in the explanation of the present invention means complex protein found in red blood cells that contains an iron molecule. That is, hemoglobin is an iron-containing oxygen-transport metalloprotein in the red blood cells of all vertebrates as well as the tissues of some invertebrates. The glucose is commonly called grape sugar, and a kind of sugar having aldehyde group. The glucose in the brain, nerve and lung tissues is essential as an energy source, and may cause convulsion if lacked by being sensitively reacted to glucose concentration in the blood. It may be possible to grasp a short-term blood sugar by measuring glucose in the blood.

HbA1c is a type of hemoglobin (blood pigment) used for learning concentration of blood sugar in the blood in a long period. As the life expectancy of red blood cells is 120 days, and after the blood glucose level rises, it will combine with the hemoglobin forming HbA1c.

If blood sugar is not properly controlled for diabetes, the HbA1c level may rise. The red blood cells generated with saccharification are shortened in life and HbA1c can reflect a person's average blood sugar over the last 3 months. Thus, if glucose level in blood is measured, a short-term blood sugar level can be learned, and if the HbA1c level is measured, and if percentage concentration (% concentration) of HbA1c is measured, to be specific, HbA1c may be a test that will tell doctors a person's long-term blood sugar for about 3 months.

The cartridge (100) according to an exemplary embodiment of the present invention as illustrated in FIG. 1 may include a blood injection unit (110), an elution unit (120), an elution solution supply unit (130), a first measurement unit (140), a second measurement unit (150), a third measurement unit (160), a glucose oxidase injection unit (170) and a detection electrode (180).

The blood injection unit (110) functions to receive blood from a user. That is, the blood injection unit (110) receives target blood for analysis through an inlet exposed to outside, and the injected blood becomes a subject for analysis. Meantime, the blood injection unit (110) includes lysis (hydrolysis) solution and zinc, and the injected blood is mixed with the lysis solution and zinc. The lysis solution functions to disintegrate cell walls of red blood cells in the blood, and the zinc functions to easily elute glucose.

The elution unit (120) functions to elute glucose and hemoglobin from the blood injected by the injection unit (110). The elution unit (120) includes membrane where the membrane may be formed in a single layer or a plurality of layers. The configuration of elution unit (120) will be described in detail later.

First, the elution unit (120) elutes glucose through the membrane. The glucose is not absorbed by zinc, such that blood containing the glucose drops and is eluted. The eluted glucose is moved to the first measurement unit (140). Meanwhile, the elution unit (120) receives the elution solution from the elution solution supply unit (130, described later) and supplies the elution solution to the blood remaining in the membrane. Then, the blood remaining in the membrane, that is, the blood except for glucose, drops down the membrane, which now flows into the second measurement (150) or the third measurement unit (160).

The elution solution supply unit (130) serves to supply the elution solution so that material mixed with the zinc that remains in the membrane, as explained above, can be eluted from the membrane. The elution solution may be such material as PBS (Phosphate Buffered Saline).

The first measurement unit (140) is a place to which the eluted glucose moves. The first measurement unit (140) optically measures the eluted glucose using an optical method. The optical measurement method may include any conventional measurement method. For example, the optical method may be such that a sample is reacted for measuring concentration of glucose and absorbance is obtained using LED and photodiode. That is, a light of particular wavelength is irradiated and concentration of glucose can be learned using light quantity that is absorbed and remained, where glucose oxidase reaction is performed to thereafter measure the concentration of glucose using the optical method.

The glucose oxidase reaction is that glucose reacts with enzyme and water in the solution to become gluconic acid and H2O2, and H2O2 oxidatively condenses Phenol and 4-Aminoantipyrine to generate quinone type red pigment.

Figure 2:
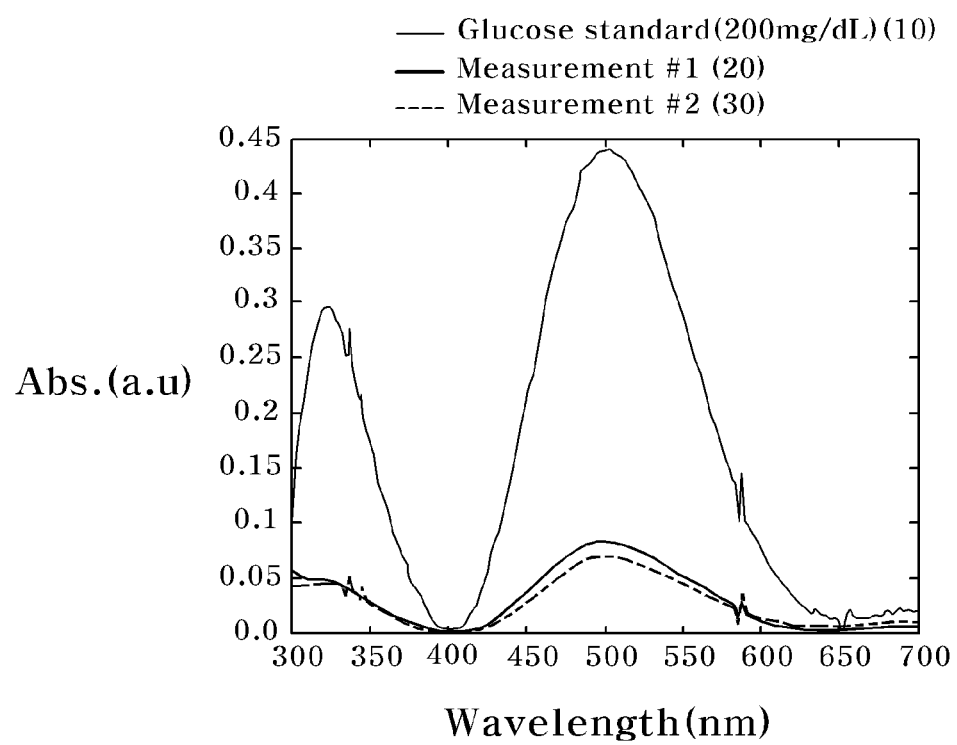
FIG. 2 is a graph illustrating a method for measuring concentration of glucose using an optical method in a cartridge according to an exemplary embodiment of the present invention.

FIG. 2 is a graph illustrating a method for measuring concentration of glucose using an optical method in a cartridge according to an exemplary embodiment of the present invention, where reference numeral 10 is a reference curve that has 200 mg/dL concentration. The vertical axis in the graph represents absorbance, and the horizontal axis represents light wavelength that is applied. If the graph is such that absorbance is measured by irradiating light of 500 nm wavelength and results thereof are indicated as reference numerals 20 and 30, concentration can be learned by comparison with the reference curve.

The second measurement unit (150) functions to measure the concentration of HbA1c from eluted hemoglobin. The second measurement unit (150) is connected to the detection electrode (180) to measure the concentration of HbA1c using electrochemical method. The process of measuring the concentration of HbA1c using the electrochemical method will be described with reference to FIG. 3.

Figure 3:
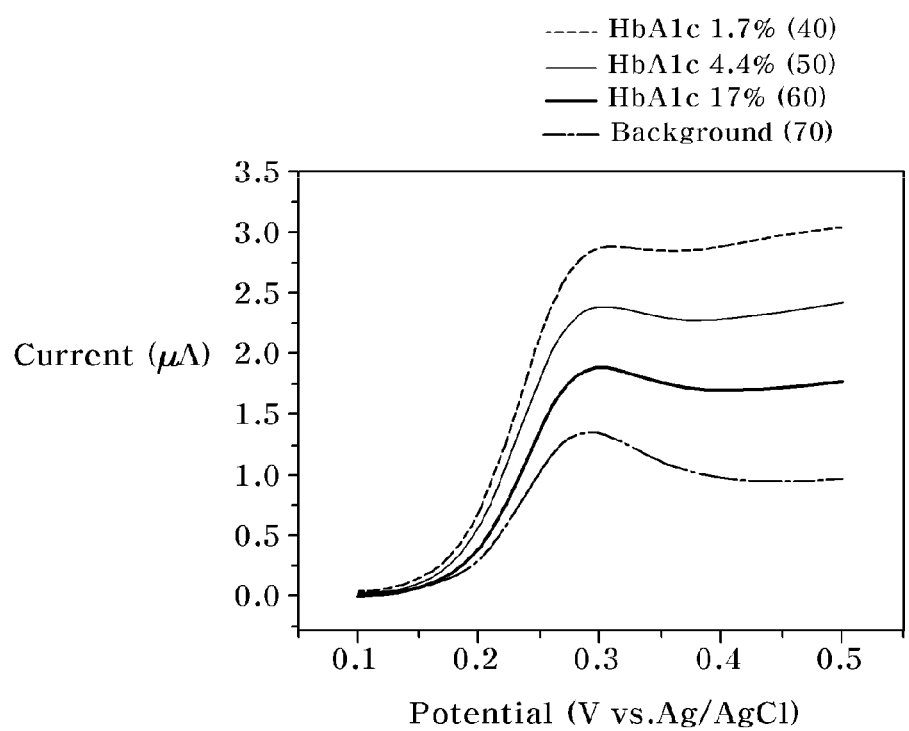
FIG. 3 is a graph illustrating a method for measuring concentration of HbA1c using an electrochemical method in a cartridge according to an exemplary embodiment of the present invention.

FIG. 3 is a graph illustrating a method for measuring concentration of HbA1c using an electrochemical method in a cartridge according to an exemplary embodiment of the present invention, where the vertical axis represents intensity of applied voltage, and the horizontal axis represents intensity of current that has flown in response to the voltage. The curves with reference numerals 40, 50, 60 represent each % concentration of HbA1c at 1.7%, 4.4% and 17%. The reference numeral 70 represents reference value. In the graph, if a 0.4V of voltage is applied, and intensity of the current thereof is measured, the % concentration of HbA1c can be learned. The % concentration represents a ratio of concentration of HbA1c in the total concentration of the hemoglobin, where the total concentration of hemoglobin is measured by the third measurement unit (160, described later). That is, the % concentration of HbA1c may be obtained by the following Equation.

$$HbA1c(\%) \text{ concentration} = \frac{HbA1c \text{ concentration}}{\text{Total } Hb \text{ concentration}} \quad [\text{Equation 1}]$$

The third measurement unit (160) functions to measure a total concentration by collecting the eluted hemoglobin. The third measurement unit (160) also measures the total concentration using the optical method as in the first measurement unit (140).

Figure 4:
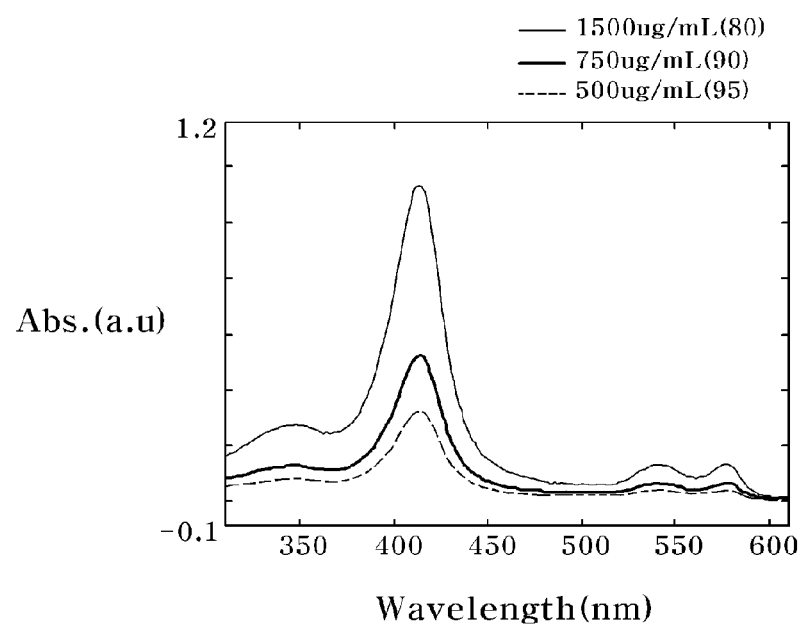
FIG. 4 is a graph illustrating a method for measuring a total concentration of hemoglobin using an optical method in a cartridge according to an exemplary embodiment of the present invention.

The graph of FIG. 4 shows similar aspect as that of FIG. 2. The curve 80 in the graph represents relationship between wavelength and absorbance of irradiated light at concentration of 1500 μg/mL, and reference numerals 90 and 95 represent the relationship at concentration of 750 μg/mL and 500 μg/mL respectively. Thus, the total concentration can be obtained if light of 414 nm whose change is the greatest is irradiated to measure the absorbance.

The glucose oxidase injection unit (170) serves to supply, to the HbA1c, glucose oxidase for detecting, by the second measurement unit (150), the electrochemical reaction. That is, the glucose oxidase injection unit (170) supplies the glucose oxidase to an entrance to the second measurement unit (150) to allow HbA1c and the glucose oxidase to be mixed. The detection electrode (180), as explained above, is formed at the second measurement unit (150) to measure the electrochemical reaction.

The cartridge according to an exemplary embodiment of the present invention can enhance efficiency in management of diabetes, because glucose having short-term blood sugar information and HbA1c having long-term blood sugar information can be simultaneously detected using a single cartridge.

Figure 5:
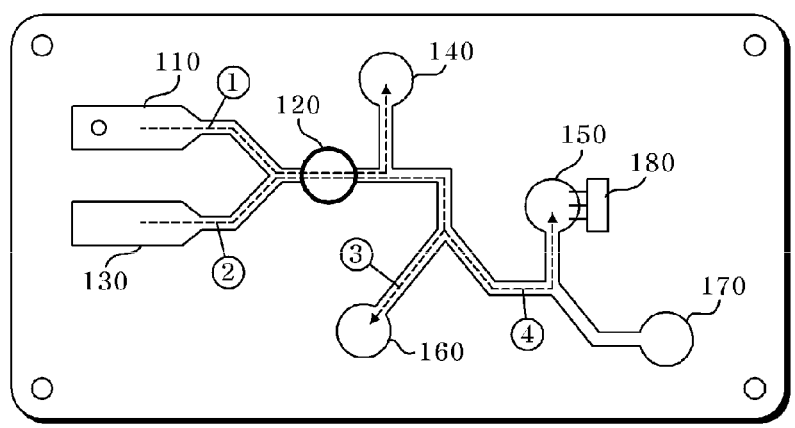
FIG. 5 is a schematic view illustrating flow of blood or reaction material in a cartridge according to an exemplary embodiment of the present invention.

FIG. 5 is a schematic view illustrating flow of blood or reaction material in a cartridge according to an exemplary embodiment of the present invention, where only the flow of blood (or material inside the blood) and reaction material are explained and each element will not reiterated.

Figure 6:
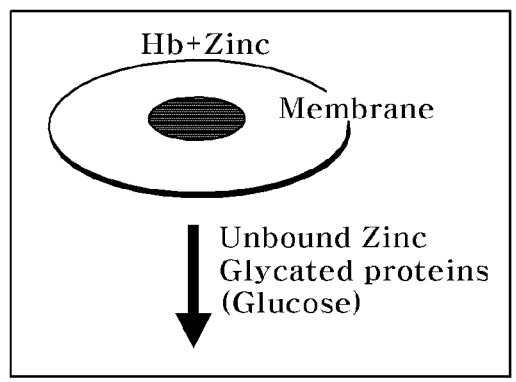
FIGS. 6 and 7 are schematic views illustrating operation of elution unit of a cartridge according to an exemplary embodiment of the present invention.

The configuration in FIG. 5 is identical to that of FIG. 1. A path ① in FIG. 5 shows the movement of injected blood. The blood injected through the blood injection unit (110) moves toward the elution unit (120). At this time, the blood injection unit (120) is connected to a syringe pump to push out the blood using air pressure. Meantime, the blood injection unit (110) supplies the hydrolysis solution and zinc to the injected blood to allow the elution unit (120) to elute the blood. That is, as illustrated in FIG. 6, although the blood component absorbed with the zinc remains in the membrane, the glucose that is not absorbed with the zinc escapes the membrane. That is, the membrane is first filtered by the elution unit (120).

Figure 7:
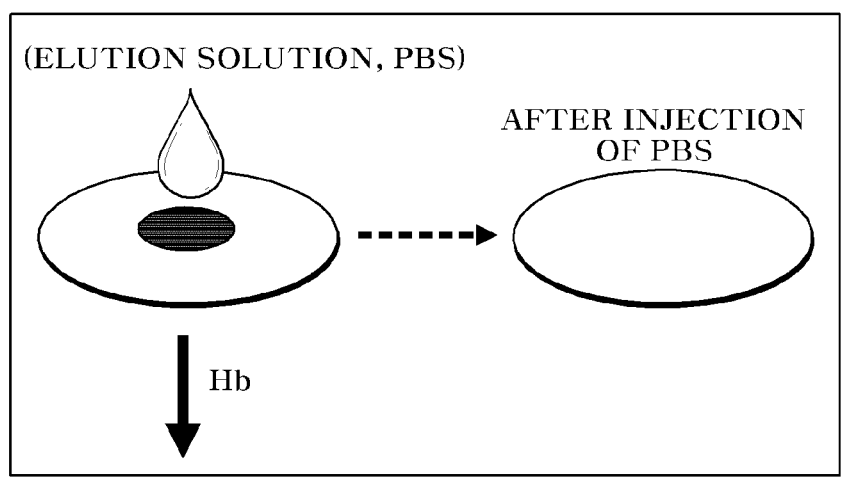

Meanwhile, the glucose eluted along the path ① moves to the first measurement unit (140), and the hemoglobin eluted along the path ① flows to the third measurement unit (160) through a path ③ by phosphate buffer supplied along a path ② (described later), or moves to the second measurement unit (150) through a path ④. The path ② illustrates movement of elution solution such as the phosphate buffer, for example. The elution solution, as illustrated in FIG. 7, elutes, from the membrane, the blood remaining in the membrane of the elution unit (120) and where the glucose is eluded, from the membrane, and moves the blood through the path ③. As illustrated in FIG. 7, the blood remaining in the membrane may be detached from the membrane by the elution solution and may move in a liquefied state.

The path ③ shows movement of hemoglobin to the third measurement unit (160) for measurement of total concentration of the hemoglobin. The hemoglobin moved to the third measurement unit (160) is analyzed by the optical method as explained before. The path ④ is a path for measuring the concentration of HbA1c. That is, the HbA1c that has reached the second measurement unit (150) can measure the concentration in the blood using the electrochemical method.

According to the method thus mentioned, the concentration of glucose can be measured by one kit, and a total concentration of the hemoglobin and concentration of HbA1c can be obtained as well, whereby the % concentration of HbA1c can be learned. The % concentration of HbA1c includes long-term blood sugar information to thereby be very useful in checking the health of a diabetic.

Figure 8:
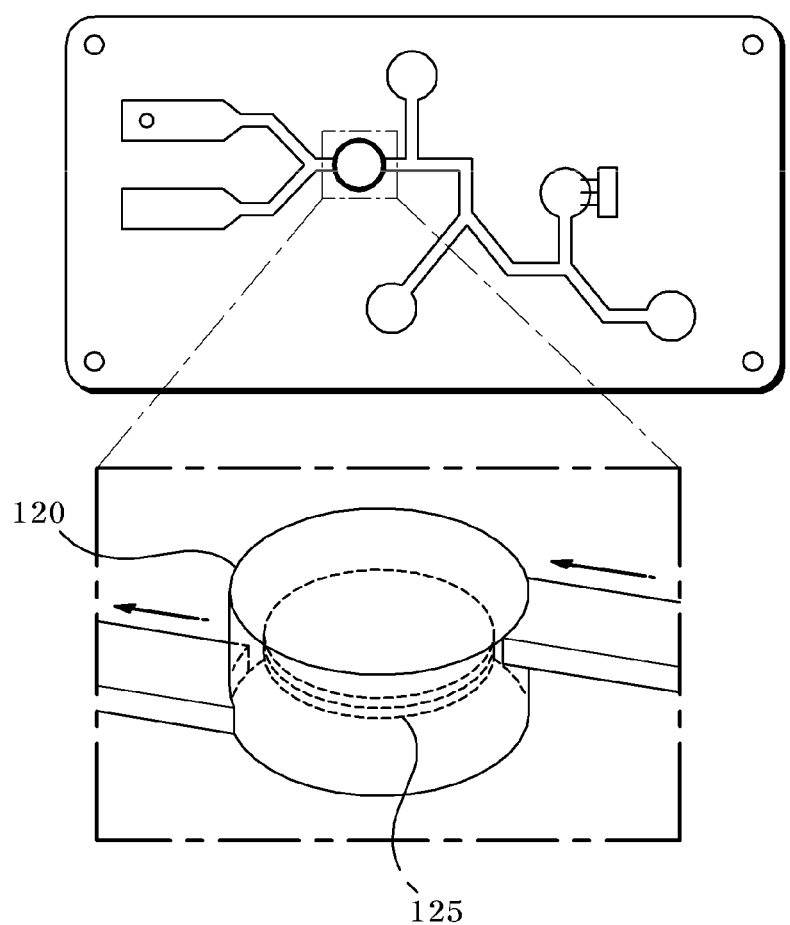
FIG. 8 is an enlarged view illustrating an elution unit of a cartridge according to an exemplary embodiment of the present invention.

FIG. 8 is an enlarged view illustrating an elution unit of a cartridge according to an exemplary embodiment of the present invention.

Referring to FIG. 8, the elution unit (120) is connected to a path in which the injected blood and elution solution move, and may include a membrane (125). The membrane (125) may include nitrocellulose compound. Meantime, the membrane (125) may be formed in two layers, where a first layer may be formed with the nitrocellulose and a second layer may be formed with nylon material.

The elution unit (120) functions to remove a backward phenomenon due to a separation structure from a relevant path at a crossroad, when fluid moves at each path. Furthermore, the elution unit (120) may remove leakage of chips that is caused by phenomenon where a high pressure is applied when the membrane (125) passes. The two-layered membrane (125) can enhance the efficiency of filtering the membrane. The following Table 1 is a graph showing a filtering efficiency of membrane (125) formed in two layers.

TABLE 1

|  | Evaluation method | Injected blood | Blood having passed membrane | Removal rate |
|---|---|---|---|---|
| glucose | spectroscopy | 44.4 ± 2.7 mg/dL | 1.8 ± 0.6 mg/dL | 95% |
|  | Blood sugar level checker | 59 mg/dL | LOW |  |
| zinc | ICP-OES | 4.31 mM | 0.13 mM | 96% |

As illustrated in Table 1, 95% of glucose that has passed the two-layered membrane (125) according to the present invention is removed and 96% of zinc is removed whereby the filtering efficiency is very high.

Figure 9:
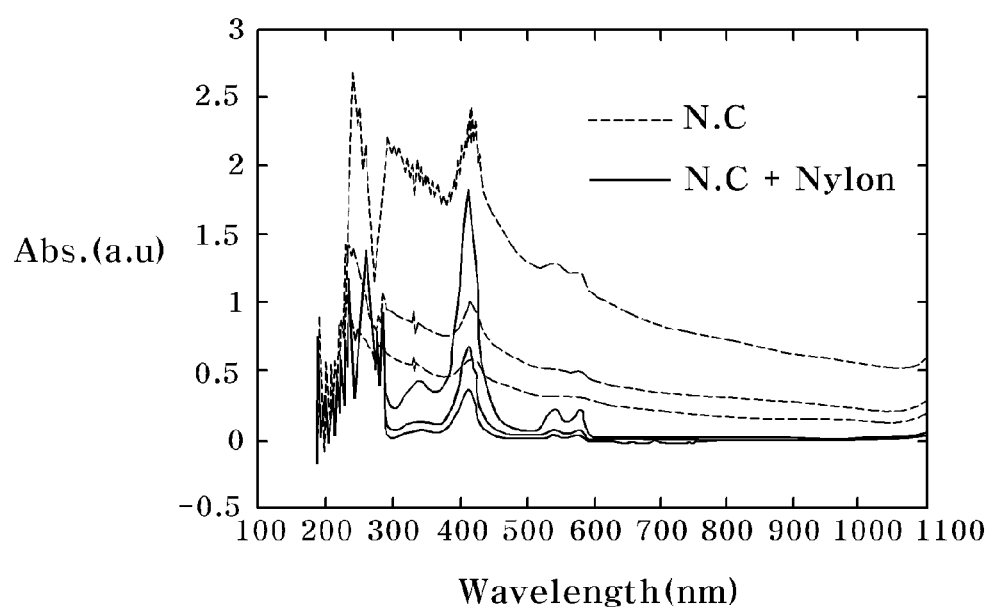
FIG. 9 is a graph illustrating an effect of elution unit of a cartridge elution unit of a cartridge according to an exemplary embodiment of the present invention.

As illustrated in the graph of FIG. 9, it is much easier to use the levels when the membrane (125) is formed with two layers than when the membrane (125) is formed with a single layer. That is, when the membrane (125) is formed with a single layer, and when the concentration is measured using the optical method, a certain degree of inclination as shown in a dotted curve is formed to require change in raw data when the levels are applied. However, when the membrane (125) is formed with two layers, an inclination-free curve can be obtained as shown in a full line. Thus, it is possible to measure the concentration using the raw data as it is to thereby prevent the measured signal from being lost. That is, noise can be removed using the optical method.

The following Table 2 shows an effect by the cartridge according to an exemplary embodiment of the present invention. It can be noted that the glucose eluted by the cartridge (100) according to an exemplary embodiment of the present invention has no great difference over the conventional blood sugar level checker in terms of measurement reliability.

TABLE 2

| Glucose level measured by conventional blood sugar level checker | Glucose level measured by present invention |
|---|---|
| 52 | 55.53 |
| 59.58 | 52.51 |
| 55.57 | 57.52 |

(unit: mg/dL)

As illustrated in Table 2, the cartridge (100) according to an exemplary embodiment of the present invention has shown accuracy not greatly different from the conventional blood sugar level checker.

Thus, the cartridge (100) according to an exemplary embodiment of the present invention can realize the same performance as that of the conventional blood sugar level checker in measuring the glucose, and can perform a long-term blood sugar management as well.

The above explanation has introduced the measurement methods by the first, second and third measurement units (140, 150, 160) in the manner of optical method or electrochemical method. However, the present invention is not limited thereto because the method is introduced as an example for the sake of convenience, and therefore, it should be apparent to the skilled in the art that the first measurement unit (140) using an optical method may be measured by electrochemical method.

Figure 10:
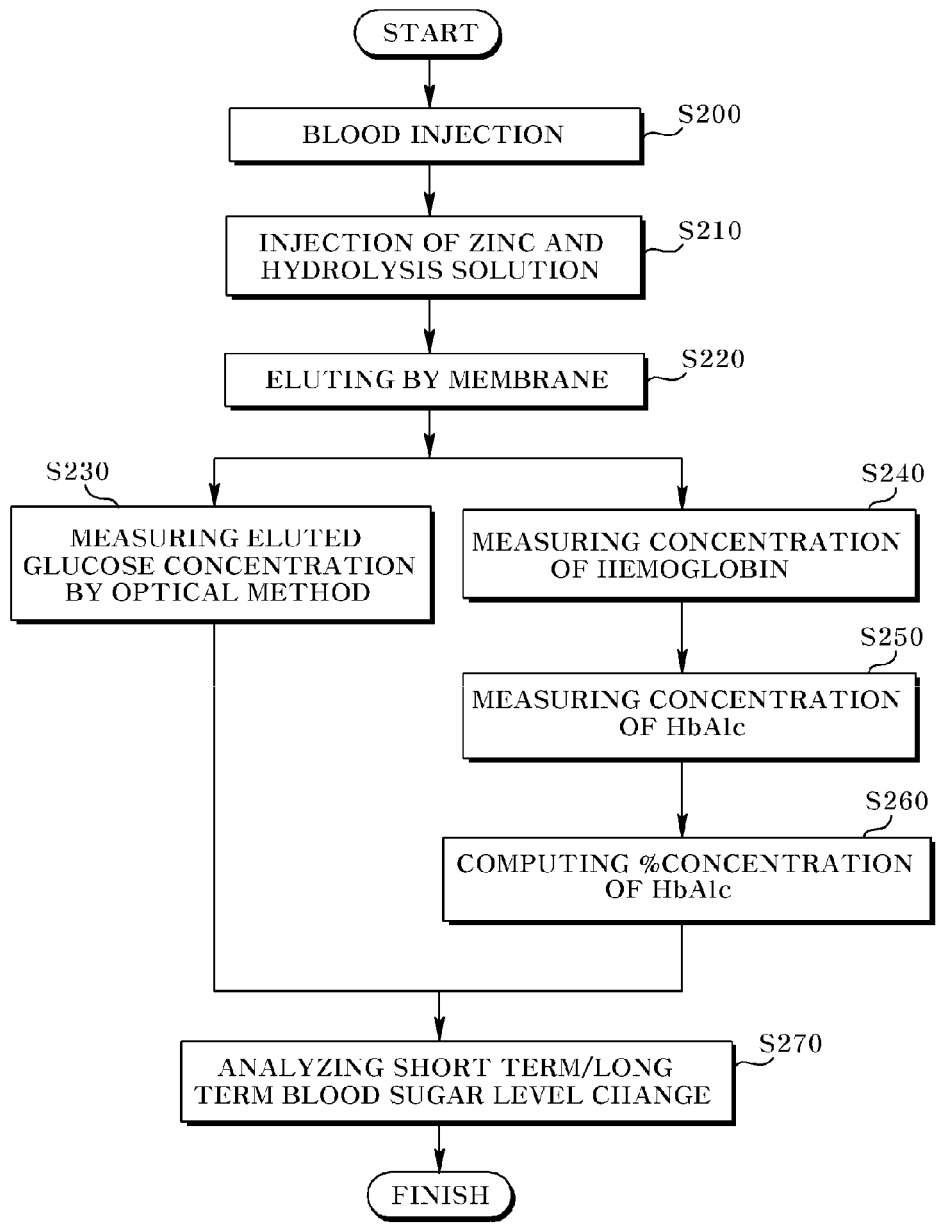
FIG. 10 is a flowchart illustrating order of blood detection method according to an exemplary embodiment of the present invention.

FIG. 10 is a flowchart illustrating order of blood detection method according to an exemplary embodiment of the present invention, where configuration of cartridge will be omitted in explanation because it is identical to that of the previous illustration.

First, blood is injected (S200). Zinc and hydrolysis solution are inserted to the injected blood (S210). Successively, the glucose is eluted using the membrane (S220). Concentration of eluted glucose is measured using an optical method (S230), the detailed processes of which are already explained as above.

Then, a total concentration of the eluted hemoglobin is measured (S240). An elution solution is injected to elute the hemoglobin. Successively, only the concentration of HbA1c is separately measured (S250). % concentration of HbA1c is computed using the total concentration of hemoglobin and the concentration of HbA1c (S260). A long-term blood sugar change is analyzed using the % concentration of HbA1c, and a short-term blood sugar change is analyzed using the concentration of hemoglobin.

The previous description of the present invention is provided to enable any person skilled in the art to make or use the invention. Various modifications to the invention will be readily apparent to those skilled in the art, and the generic principles defined herein may be applied to other variations without departing from the spirit or scope of the invention. Thus, the invention is not intended to limit the examples described herein, but is to be accorded the widest scope consistent with the principles and novel features disclosed herein.

INDUSTRIAL APPLICABILITY

The glucose and HbA1c detecting method and a cartridge using the same according to the present invention have an industrial applicability in that efficiency of urine sugar management can be enhanced through simultaneous detection of glucose having short-term information on blood sugar, and HbA1c having long-term blood sugar, by using one cartridge.

The invention claimed is:

1. A cartridge, the cartridge comprising:
a blood injection unit configured to receive blood and including a hydrolysis solution and zinc, wherein the blood injection unit supplies, to the injected blood, the hydrolysis solution to disintegrate cell walls of red blood cells in the blood, and the zinc is absorbed with hemoglobin (Hb) and not absorbed with glucose inside the blood;
an elution unit configured to separate glucose and hemoglobin (Hb) from the injected blood, the elution unit including a membrane configured to filter the injected blood and pass through only the glucose, wherein the membrane includes a first layer comprising a nitrocellulose compound and a second layer comprising nylon, and the elution unit is connected to a second path extending from the membrane;
a first measurement unit including an optical measuring instrument comprising a photo diode and configured to measure concentration of the glucose, wherein the first measurement unit measures a concentration of the glucose using an optical method subsequent to performance of a glucose oxidase reaction;
an elution solution supply unit including phosphate buffered saline solution and connected to the elution unit by a first path, the elution solution supply unit configured to supply the phosphate buffered saline solution for eluting the hemoglobin absorbed with the zinc from the membrane and passing the eluted hemoglobin through the membrane;
a second measurement unit including a detection electrode and configured to measure a concentration of HbA1c in the hemoglobin in an electrochemical method; and
a third measurement unit including an optical measuring instrument comprising a photo diode and configured to measure a total concentration of the eluted hemoglobin by being connected to the second path through which fluid flows between the first measurement unit and the second measurement unit,
wherein the first measurement unit, the third measurement unit, the second measurement unit and a glucose oxidase injection unit are sequentially connected to the second path, the glucose oxidase injection unit including a glucose oxidase and connected to an entrance to the second measurement unit to allow the HbA1c and the glucose oxidase to be mixed.

2. The cartridge of claim 1, wherein the elution unit further includes an O-ring configured to fix the membrane.

3. The cartridge of claim 1, wherein the glucose oxidase has an electrochemical activity to the HbA1c in order to measure the concentration of the HbA1c by an electrochemical method.

4. The cartridge of claim 1, further comprising an analyzer configured to analyze blood sugar changes in the injected blood by computing a percentage concentration (% concentration) of the HbA1c based on a result of the second measurement unit and a result of the third measurement unit.

5. The cartridge of claim 1, wherein the first measurement unit and the second measurement unit are downstream of the elution unit.

6. The cartridge of claim 1, wherein the elution solution supply unit is upstream of the elution unit.

7. A cartridge, the cartridge comprising:
a blood injection unit receiving blood including a hydrolysis solution and zinc and receiving blood, wherein the blood injection unit supplies, to the injected blood, the hydrolysis solution to disintegrate cell walls of red blood cells in the blood, and the zinc is absorbed with hemoglobin (Hb) and not absorbed with glucose inside the blood;
a membrane separating glucose and hemoglobin (Hb) from the injected blood and passing through only the glucose;
an elution solution supply unit connected to the membrane by a first path, the elution solution supply unit supplying an elution solution for eluting the hemoglobin from the membrane and passing the eluted hemoglobin through the membrane;
a first measurement unit including an optical measuring instrument comprising a photo diode to measure a concentration of the glucose, the membrane being between the blood injection unit and the first measurement unit;
a second measurement unit including a detection electrode configured to measure concentration of HbA1c in the eluted hemoglobin in an electrochemical method; and
a third measurement unit including an optical measuring instrument comprising a photo diode to measure a total concentration of the eluted hemoglobin,
wherein the membrane includes a first layer comprising nitrocellulose compound and a second layer comprising nylon, and
wherein the first measurement unit, the third measurement unit, the second measurement unit and a glucose oxidase injection unit are sequentially connected to a second path extended from the membrane, the glucose oxidase injection unit configured to supply a glucose oxidase to an entrance to the second measurement unit to allow the HbA1c and the glucose oxidase to be mixed by being connected to the second measurement unit.

* * * * *